US007746466B2

(12) United States Patent
Godin et al.

(10) Patent No.: US 7,746,466 B2
(45) Date of Patent: Jun. 29, 2010

(54) SYSTEM AND METHOD FOR FLOW CYTOMETRY

(75) Inventors: Jessica Godin, San Diego, CA (US); Yu-Hwa Lo, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/152,665

(22) Filed: May 14, 2008

(65) Prior Publication Data

US 2009/0027666 A1    Jan. 29, 2009

Related U.S. Application Data

(60) Provisional application No. 60/917,848, filed on May 14, 2007, provisional application No. 61/068,198, filed on Mar. 5, 2008.

(51) Int. Cl.
*G01N 21/01* (2006.01)
*C12M 1/34* (2006.01)

(52) U.S. Cl. .............................. 356/246; 435/6; 435/39; 435/286.5; 250/458.1

(58) Field of Classification Search ......... 356/432–444, 356/244, 246, 484, 480; 250/251, 458.1, 250/462.1, 227.19; 436/5, 8, 10, 63, 66, 436/164, 165, 68.1; 435/39, 286.5, 34, 288.7
See application file for complete search history.

(56) References Cited

U.S. PATENT DOCUMENTS 6,493,090 B1 * 12/2002 Lading et al. ................ 356/484
6,815,664 B2 * 11/2004 Wang et al. .................. 250/251
6,867,420 B2 *  3/2005 Mathies et al. ........... 250/458.1
6,972,173 B2 * 12/2005 Su et al. ......................... 435/6
7,038,856 B2    5/2006 Quake et al.
7,179,423 B2 *  2/2007 Bohm et al. ................. 422/100

(Continued)

FOREIGN PATENT DOCUMENTS

WO    WO20070403313    4/2007

(Continued)

OTHER PUBLICATIONS

S. Camou, et al., Lab Chip, 2003, 3, 40-45.

(Continued)

*Primary Examiner*—Sang Nguyen
(74) *Attorney, Agent, or Firm*—Fish & Richardson P.C.

(57) ABSTRACT

A flow cytometry system and related method, among other things, are disclosed. In at least one embodiment, the system includes first, second, and intermediate slab formations, the last of which has formed therewithin a microfluidic channel, a lens structure arranged proximate the microfluidic channel, and a light conveying structure arranged proximate to the lens structure. The lens structure is configured to direct a portion of light to proceed between the channel and the conveying structure. The intermediate slab formation is sandwiched between the other two slab formations. In at least another embodiment, the system includes a microfluidic prism arranged proximate to the second end of a light conveying structure. Light emanating from a microfluidic channel is provided to the conveying structure at the first end, conveyed to the second end, and provided to the prism, which outputs a plurality of portions of the light at different frequencies in different directions.

20 Claims, 8 Drawing Sheets

U.S. PATENT DOCUMENTS

| | | | |
|---|---|---|---|
| 7,241,988 B2* | 7/2007 | Gruber et al. | 250/251 |
| 7,418,169 B2* | 8/2008 | Tearney et al. | 385/25 |
| 2002/0127563 A1* | 9/2002 | Salafsky | 435/6 |
| 2004/0009516 A1* | 1/2004 | Nelson et al. | 435/6 |
| 2005/0161326 A1* | 7/2005 | Morita et al. | 204/450 |
| 2008/0213821 A1* | 9/2008 | Liu et al. | 435/39 |

FOREIGN PATENT DOCUMENTS

| | | |
|---|---|---|
| WO | WO2007051170 | 12/2007 |

OTHER PUBLICATIONS

Y. Gambin, Applied Physics Letters 88, 2006,174102, 3 pages.

J. Godin, et al., Applied Physics Letter, 89, 2006, 061106, 3 pages.

J. Seo, et al., Sensors and Actuators B 99 (2004), pp. 615-622.

Z Wang, et al., Lap Chip, 2004, 4, 372-377.

Godin, Jessica et al., Integrated Fluidic Photonics for Multi-Parameter In-Plane Detection in Microfluidic Flow Cytometry, IEEE, Ontreal, Canada, Oct. 30-Nov. 2, 2006, pp. 605-606, WT3.

Godin, Jessica et al., Two Dimensional Lenses Microfabricated in PDMS for Integrated Fluidic Photonic Devices, Optical Society of America, Washington, DC, 2006.

Godin, Jessica et al., Microfluidic Flow Cytometer with On-Chip Lens Systems for Improved Signal Resolution, IEEE Sensor, 2007.

Godin, Jessica et al., Integrated Microfluidic Photonic Sensors, IEEE/LEOS, Summer Topical Meetings, IEEE, 2007.

Bang, H. and H. Yun, "Expansion channel for microchip flow cytometers," Lab of a Chip 6(10) 1381-1383 (2006).

Givan, A.L., Flow Cytometry; First Principles, 2nd Edition, New York: Wiley-Liss, 2001, pp. 25-30.

Godin, G. et al., "Single Particle High Resolution Spectral Analysis Flow Cytometry," Cytometry Part A 69A: 842-851 (2006).

Lien, V. et al., "A Prealigned Process of Integrating Optical Waveguides with Microfluidic Devices, " IEEE Photon. Tech. Lett. 16(6): 1525-1527, 2004.

Shapiro, H.M., Practical Flow Cytometry,4th Edition, Hoboken, New Jersey, John Wiley & Sons, Inc., 2003, pp. 2-11.

* cited by examiner

SYSTEM AND METHOD FOR FLOW CYTOMETRY

CROSS-REFERENCE TO RELATED APPLICATIONS

This application claims the benefit of U.S. provisional patent application No. 60/917,848, entitled "Light Conveying Device" filed on May 14, 2007, and further claims the benefit of U.S. provisional patent application No. 61/068,198, entitled "System and Method for Flow Cytometry" filed on Mar. 5, 2008, and both of the aforementioned U.S. provisional patent applications are hereby incorporated by reference herein.

STATEMENT REGARDING FEDERALLY SPONSORED RESEARCH OR DEVELOPMENT

This invention was made with United States Government support awarded by the following agency: Air Force Office of Scientific Research (AFOSR) Grant No. F49620-02-1-0288. The United States Government has certain rights in this invention.

FIELD OF THE INVENTION

The present invention relates to optical devices and, more particularly, relates to devices for conveying and/or sensing light, for example, devices that convey and sense light emissions from cells, particles or other material suspended within fluid as in the case of flow cytometry devices.

BACKGROUND OF THE INVENTION

Flow cytometry devices are commonly employed to measure physical and/or chemical properties of particles such as cells (or other material) that are suspended in a fluid stream. Such information can be of significant value in a variety of circumstances. For example, doctors can utilize information derived using flow cytometry devices to obtain information regarding their patients' blood counts, white blood cell counts, leukemia progression and other characteristics. Also for example, flow cytometry devices can be used to conduct biological research, and for a variety of other purposes. A long standing commercial objective has been to reduce the complexity and cost of flow cytometry systems in order to make them more attractive for certain routine clinical diagnostic applications, such as HIV AIDS diagnosis and therapy monitoring. One pressing need for simpler, low-cost systems exists in Africa and Asia, where significant funds from organizations such as the WHO and the Gates Foundation are now available for the purchase of therapeutic drugs, but the availability of these expensive drugs is limited and the drugs are rationed based upon strict WHO diagnostic criteria that involve measurement of the patient's lymphocyte sub-populations (primarily CD4/CD8 counts and ratios).

Flow cytometry devices operate by shining light that is well-collimated (sometimes but not necessarily from a laser) onto a fluid passage through which is flowing a fluid carrying the cells (or other particles or material) of interest. Upon encountering the cells the light is scattered or absorbed. Depending upon the amount (and directions) of scattering and on the amount and color of the induced fluorescence, information can be determined about the characteristics of the cells. In addition, in many benchtop flow cytometry systems, dichroic mirrors are employed for separating fluorescence signals by wavelength. Optical filters are additionally used in such systems for selectively passing a particular wavelength band of interest to a detector. Typically, such systems employing dichroics and optical filters are bulky systems having multiple parts, which increase the complexity and cost of such cytometry systems. Thus, while at this time there remains a great need for information that can be reliably obtained through flow cytometry techniques, the relatively high complexity and costs of conventional flow cytometry techniques limit their use largely to laboratories within major metropolitan areas.

While many conventional flow cytometry systems are generally large, complicated and expensive devices insofar as the systems typically employ lasers, specialized lenses, expensive (e.g., quartz) glass flow tubes, and multiple photomultiplier tubes (PMTs), some attempts have also been made to develop smaller, less complicated, and less expensive systems. One type of system employs a transparent microfluidic channel through which flow the cells (or other particles or material) of interest, and polymer waveguides or fiber optics arranged along sides of the channel that are capable of directing light to, or conducting light away from, the channel. In at least some such systems, lenses are employed between the waveguides and the sides of the microfluidic channels so as to focus light directed toward the microfluidic channels.

Although such systems employing microfluidic channels and waveguides are potentially smaller and less expensive than many other types of conventional systems, systems of this type have certain disadvantages. In particular, because of the relative sizes of the waveguides, microfluidic channels and/or lenses in such systems, it is difficult to position multiple waveguides proximate a given microfluidic channel in such a way as to gather light emanating from the channel in different directions, such that it is difficult to gather multi-parameter data. Further, while the lenses are useful for guiding at least some of the light emanating from the channel, a significant amount of the light emanating from the channel nevertheless typically is lost as it passes over or under the waveguides. Also, it is often difficult to separate out or distinguish desired components of light emanating from a channel from other light components. Further, it is often difficult to control the positioning and speed of movement of sample materials of interest (e.g., cells, other biological materials, particulate matter) through the microfluidic channel and past one or more sensors in a manner that facilitates optical sensing of those materials of interest and results in the generation of useful optical data.

For at least these reasons, it would be advantageous if an improved system employing microfluidic channel(s), waveguide(s) and lens(es) could be developed that could be implemented as part of a microfluidic photonic sensor system for use in flow cytometry applications and/or other applications. It further would be advantageous if, in at least some embodiments, such an improved system allowed for better sensing of light emanating from a given microfluidic channel in a variety of directions, and/or was more efficient in directing light to the waveguides. It would additionally be advantageous if, in at least some embodiments, it was possible to separate out or distinguish among different portions of light of different spectra emanating from a microfluidic channel, without the complexity and cost associated with the use of dichroics, optical filters and the like. It would further be advantageous if, in at least some embodiments, it was possible to better control the positioning and movement of materials of interest within a sample for enhanced optical sampling.

SUMMARY OF THE INVENTION

The present inventors have recognized that in at least some embodiments a microfluidic channel, one or more waveguides and one or more lenses can all be implemented on a single chip having slab formations above and below the channel, waveguide(s) and lens(es). By appropriately choosing the refractive index or indices of the slab formation(s), the waveguide(s), the lens(es), and the microfluidic channel can be positioned farther apart from each other than is possible in conventional embodiments, thus making it possible to arrange large numbers of waveguides and associated lenses at fixed alignment locations around a microfluidic channel and thus allowing for light sensing (e.g., sensing of scattered light, fluorescent light, or the absence of light due to light absorption) at a variety of angles around a given target point or region within the microfluidic channel to occur. In particular, the slabs allow for lenses that can be formed independently from the waveguides or the channel, and also allow for the formation of multiple lenses between the channel and any single waveguide for improved directing of light. Additionally, an appropriate choice of material for such independently-formed lenses further reduces light loss by reflection. Further, through the use of the above-mentioned slab formations, the loss of light above and/or below the waveguide(s) as it emanates from the microfluidic channel is reduced, which corresponds to increased efficiency in directing light to the waveguides.

Thus, in at least some embodiments, the present invention relates to a system for flow cytometry. The system includes first and second slab formations, and additionally an intermediate slab formation. The intermediate slab formation has formed therewithin a microfluidic channel, a first lens structure arranged proximate the microfluidic channel, and a first light conveying structure arranged proximate to the lens structure, where the first lens structure is configured to direct at least a portion of light to proceed between the microfluidic channel and the first light conveying structure. The intermediate slab formation is sandwiched between the first and second slab formations.

The present inventors have further recognized that further systems can be developed that will allow for different portions of light of differing spectra emanating from a microfluidic channel to be separated and sensed independently (or substantially independently), without necessarily involving the use of dichroics, optical filters or other similarly complicated or costly devices. Such systems in at least some embodiments employ one or more microfluidic prisms that differentiate varying light spectra emanating from a microfluidic channel, something which can be of particular value in the case of fluorescent light emanating from the microfluidic channel. The present inventors have additionally recognized the importance of attaining desired levels of density of sampled material (e.g., cells, other biological materials, other particles, etc.), attaining desired speeds of flow of such material through a sampling zone, and limiting the amount of extraneous fluid surrounding the material of interest that can diminish the efficacy of optical sensing. To achieve such goals, the present inventors have recognized that a special re-packing system or draining system can be employed in at least some embodiments in conjunction with (or as part of) the microfluidic channel.

Thus, in at least some embodiments, the present invention relates to a system for flow cytometry. The system includes a microfluidic channel, a first light conveying structure having first and second ends, where the first end is arranged proximate to the microfluidic channel, and at least one microfluidic prism arranged proximate to the second end of the first light conveying structure. Light emanating from the microfluidic channel is provided to the first light conveying structure at the first end, conveyed by way of the first light conveying structure to the second end, and in turn provided to the at least one microfluidic prism. The at least one microfluidic prism in turn outputs a plurality of portions of the light at a plurality of different frequency ranges, respectively, in a plurality of different directions, respectively.

Additionally, in at least some embodiments, the present invention relates to a method of flow cytometry. The method includes directing a sample fluid through a microfluidic channel, directing incident light toward the sample fluid, and receiving additional light emanating from the sample fluid out of the microfluidic channel, the additional light resulting from exposure of the sample fluid to the incident light. The method further includes communicating the additional light to at least one prism, and sensing a component of the additional light output by the at least one prism, the component being one of a plurality of components of the additional light output by the at least one prism. Each of the plurality of components of the additional light is associated with a different respective light frequency range and is emitted out of the at least one prism in a different respective direction.

DETAILED DESCRIPTION OF THE PREFERRED EMBODIMENT

Figure 1:
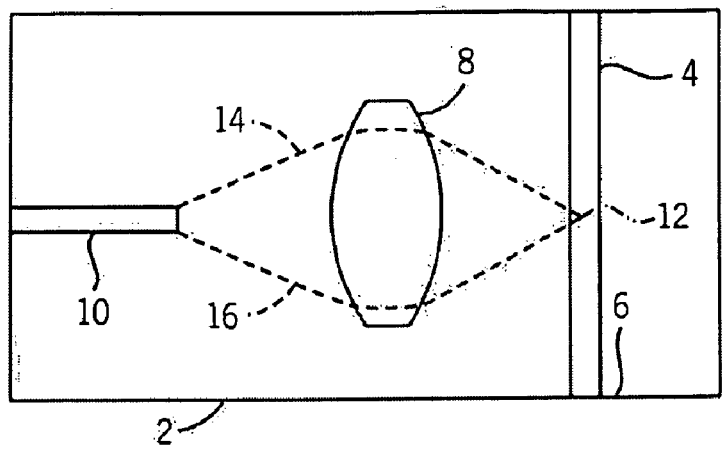
FIG. 1 is a top plan view showing, in schematic form, components of an exemplary microfluidic flow cytometer.

A top plan view of components 2 of an exemplary microfluidic flow cytometer are shown in schematic form. As shown, the cytometer components 2 include a microfluidic channel 4 that is capable of conducting fluids that can contain various biological materials such as blood cells or other types of cells, particles or possibly other types of materials. Fluid flow (as directed by a pump, gravity, or some other force) can proceed through the microfluidic channel 4 along a direction represented by an arrow 6, although the fluid can be directed in either direction depending upon the embodiment. Spaced apart to the side of the microfluidic channel 4 is a microfluidic lens 8, and additionally spaced apart from the lens is a waveguide 10. Thus, the lens 8 is between the microfluidic channel 4 and the waveguide 10, with the waveguide 10 extending away from the lens in a direction that also extends away from the channel.

As shown, the waveguide 10 in the present embodiment is orientated substantially perpendicularly with respect to the axis of the microfluidic channel 4. However, in other embodiments (and as shown, for example, in FIG. 4), the waveguide 10 can also extend away from the channel in a direction other than 90 degrees relative to the channel. Further in the present embodiment, the lens 8 is designed so that light exiting the waveguide 10 is passed through the lens 8 and as a result is then focused to a focal point (or region) 12 within the microfluidic channel 4. First and second exemplary light rays 14 and 16 illustrate exemplary light paths between the waveguide 10 and the focal point 12 via the lens 8.

It will be understood that, although FIG. 1 is intended to show light being transmitted from the waveguide to the channel, it is equally representative of a system that is implemented in reverse, that is, in which light originating at the focal point 12 of the channel 4 is collected by the lens 8 and thus conveyed to the waveguide 10. It will further be understood that the light emanating from the focal point 12 in such a manner in general will be primarily (if not entirely) scattered light or excited fluorescence that is scattered off of or emitted by the cells, particles or other material within the channel 4 after light has been directed toward the cells, particles or material from a light source (as shown in, for example, FIG. 4).

Figure 2:
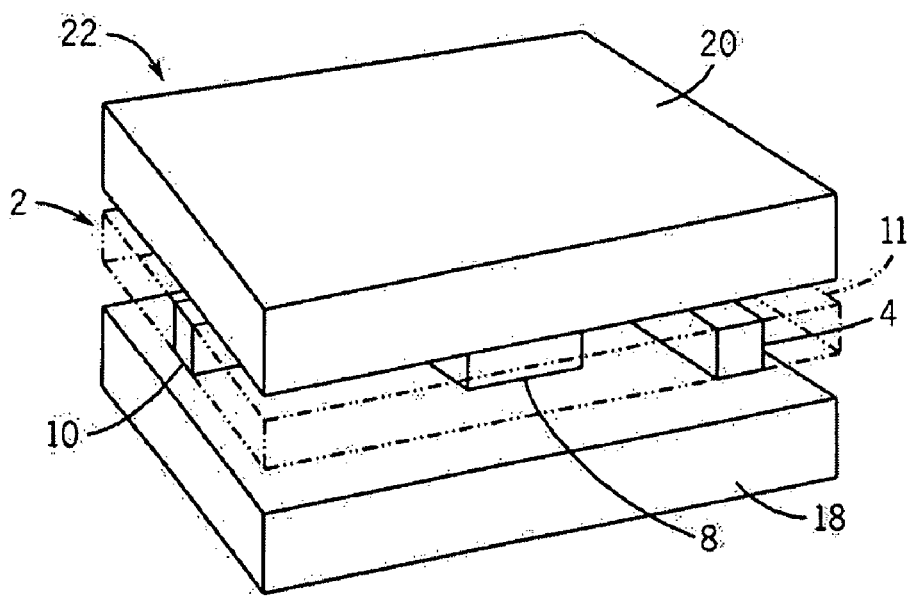
FIG. 2 is a side perspective view of the components of the flow cytometer of FIG. 1 additionally in combination with top and bottom slab formations.

Turning to FIG. 2, the components 2 of the microfluidic flow cytometer of FIG. 1 are shown in a different, side perspective view in combination with further components. More particularly, the microfluidic channel 4, lens 8, and waveguide 10 in FIG. 2 are shown to be formed as cavities within a primary slab formation (or simply primary slab) 11, which in turn is positioned upon a first additional slab 18 and beneath a second additional slab 20 so as to form an overall sandwich-like structure 22. For convenience of illustration, FIG. 2 shows the additional slabs 18, 20 to be exploded somewhat from the primary slab 11; however, it will be understood that in practice the primary slab 11 is in contact with, and sandwiched directly between, the additional slabs 18 and 20. The additional slabs 18 and 20 can be considered as cladding layers, while the primary slab 11 can be considered a core (light-guiding) layer. It will be understood that, in at least some embodiments, the lens 8 can be spaced apart from the microfluidic channel 4 and/or the waveguide 10 inside the slab 11. That is, the cavity forming the lens 8 will be separated from the cavities forming the waveguide 10 and the channel 4 by way of material of the primary slab.

The slabs 18 and 20 are made of a material (or multiple materials) that has a lower refractive index (e.g., n=1.41) by comparison with the refractive index of the material of the primary slab 11 (e.g. 1.415) and a lower refractive index than the effective core of the waveguide 10 (e.g., n=1.42 or n=1.415). Likewise, the lens 8 also has refractive index that is greater than the refractive indices of the slabs 18 and 20 (for example, n=1.67). As a result of these selected refractive indices, the slabs 18 and 20 have the effect of preventing scattered light from escaping away from the lens 8 (or at least reduce the amount of light that escapes) above and below the level of the primary slab 11 containing the microfluidic channel 4, the lens 8 and the waveguide 10. Further, the slabs 18, 20 enhance the degree to which light emanating from the lens 8 is directed into and captured by the waveguide 10 and/or directed toward the microfluidic channel 4.

Figure 3:
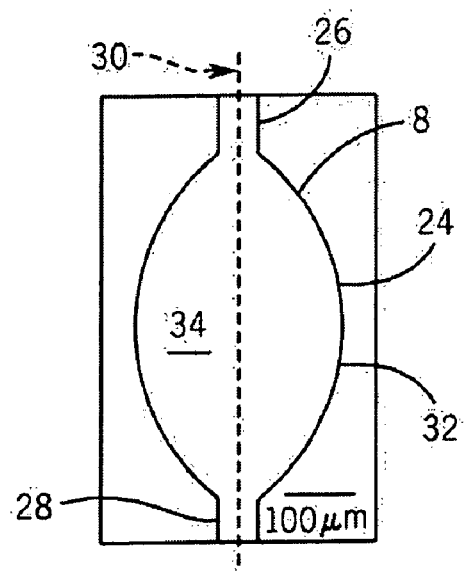
FIG. 3 shows in further detail a cross-sectional view of an exemplary lens component that can be used in the flow cytometer of FIG. 1.

An exemplary form of the lens 8 is shown in somewhat more detail in FIG. 3. As shown, the lens 8 includes an oval-shaped (or eye-shaped) lens formation 24 and first and second channels 26 and 28 respectively extending outward away from the oval-shaped lens formation 24 along its major axis 30. The lens 8 in particular has an outer shell 32 that can be formed by the primary slab 11, and which can be formed from various materials including, in the present embodiment, polydimethylsiloxane ("PDMS"). An interior 34 within the lens 8 is filled with a fluid or other material that has the desired refractive index (again, for example, n=1.67). In the present embodiment, the exact shape of the lens 8 is fixed; that is, either the shape of the outer wall 32 is hardened, or at least the amount of fluid within the cavity 34 is fixed. In alternate embodiments, it is possible that the shape of the lens 8 could be varied by employing an outer wall 32 that was flexible, by varying the amount of fluid within (or pressure of) the fluid within the cavity 34, or by alteration of the refractive index of the lens material or surrounding media by modulating temperature, applied voltage, or other factors or mechanisms. Also, in the present embodiment, each of the waveguide 10 and the microfluidic channel 4 can also be formed from PDMS or other similar materials, and the waveguide region can be with a fluid or other material that has the desired refractive index (again, for example, n=1.42). Filling of a structure such as one of the waveguides 10 with PDMS can occur by way of capillary action, among other mechanisms.

The exact configurations, sizes and/or shapes of the various components shown in FIGS. 1-3 can vary depending on the embodiment. In one embodiment, for example, the microfluidic channel 4 will have a cross sectional width of approximately 150 micrometers, the distance between the microfluidic channel and the major axis 30 of the lens will be approximately 1.3 millimeters, the distance from the major axis to the closest end of the waveguide 10 will be approximately 16.5 millimeters, the greatest width of the lens 8 as measured perpendicularly to the major axis will be approximately 0.6 millimeters, the waveguide 10 will have a cross-sectional width and depth of approximately 50 micrometers, the lens will have a radius of curvature of approximately 0.69 millimeters, and the lens will have an aperture of approximately 1 millimeter. As already noted, the lens can be filled with an optical fluid of refractive index of 1.67 (an illumination source could be a 5 mW semiconductor diode laser of 650 nm wavelength). However, the present invention is also intended to encompass a variety of other embodiments having components with a variety of different configurations, sizes and/or shapes.

The present embodiment of FIGS. 1-3 is intended to be particularly illustrative of components of a microfluidic flow cytometer that condense the optical portions of the device onto a polymer chip. The cytometer in at least some embodiments employs one or more microfabricated two-dimensional fluid-filled lenses (e.g., in an optical polymer), which can manipulate light (i.e. expand, collimate, focus) in ways analogous to bulk glass optics, but on a smaller scale. Such on-chip optics allow for device portability, less expensive optics, easier customization, lower equipment costs, reduced amounts of maintenance and alignment of components. In particular, the use of a microfabricated 'mold' for generating the polymer replicas that make up the device allows for a wide variety of lens geometries (e.g., spherical or elliptical lens faces, etc) to be generated (this is in contrast to the fabrication of bulk glass lenses with such geometries is a specialized and expensive endeavor).

Further, the on-chip lenses are beneficial in other regards as well. In particular, the on-chip lenses make side-scatter measurements possible. The on-chip lenses also allow for the same control over illumination conditions that free-space optics allows. This is desirable, since the precision and reproducibility of flow cytometer measurements depends upon on the reproducibility of illumination conditions (a focused, collimated beam is needed to ensure that each cell is illuminated in the same fashion, so that the signals can be used to establish identity relative to other cells).

The present embodiment is further illustrative of a flow cytometer that is capable of being implemented on and/or fabricated as a single chip. Such a microfluidic flow cytometer can be batch fabricated, and thus can serve as a potentially inexpensive, disposable, mass-producible and possibly portable biological instrument (a veritable "laboratory-on-a-chip"). Such a microfluidic flow cytometer allows for the use of small sample volumes (unlike conventional benchtop cytometers). The optical and fluidic portions are disposable and fabricated on a single chip, thus the device as a whole would be expected to require less servicing and cleaning, and would be lighter and more portable than a conventional benchtop counterpart. Additionally, the monolithic integration of microfluidics and the two-dimensional lenses in accordance with embodiments of the present invention can potentially be applied to many commercial devices. For example, a simple chip of this type can be used as a small-volume, disposable fluorescence assay for biological applications. With the correct wavelength or illumination power, such a device can be used to selectively damage or kill cells in a sample. The two-dimensional lenses offer potential imaging or slit-scanning applications.

Further, while the components of FIG. 1 are components that can be used to sample light emanating from the single focal point 12, the present invention is also intended to encompass many embodiments of microfluidic flow cytometers that employ multiple sets of components such as those shown in FIG. 1. In particular, in at least some embodiments, multiple waveguides can be arranged around the microfluidic channel so as to allow detection of light emanating in a variety of directions from the focal point 12 (and/or possibly even from multiple focal points along the microfluidic channel). Exemplary embodiments of devices of this type are discussed with FIGS. 4-10.

Figure 4:
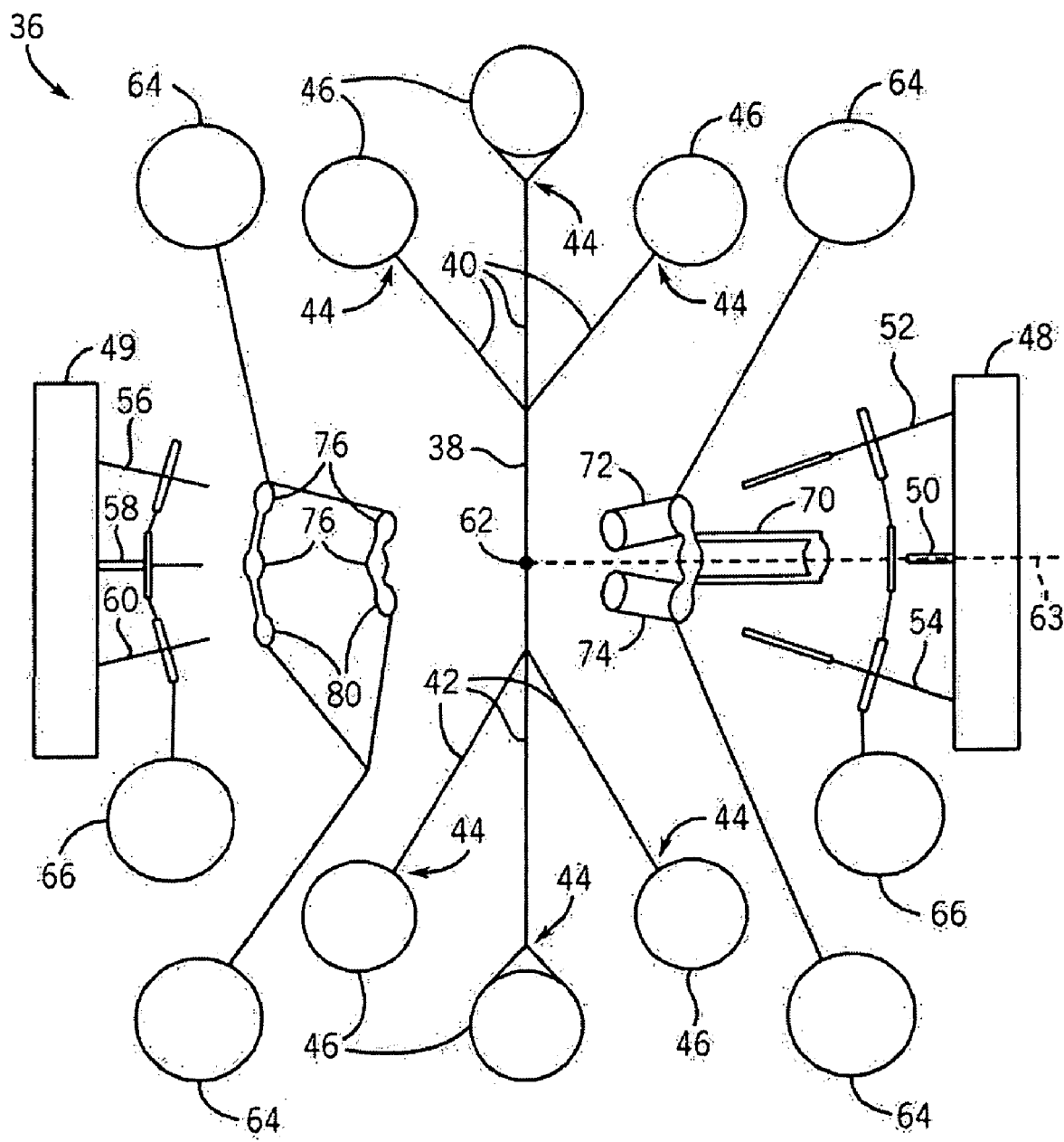
FIG. 4 is a top plan view showing, in schematic form, components of an additional exemplary microfluidic flow cytometer employing multiple lenses and multiple waveguides.

Turning to FIG. 4, exemplary components 36 of another microfluidic flow cytometer having multiple sets of components similar to those of FIGS. 1-3 are shown in a top plan view in schematic form. Although slabs such as the slabs 11, 18, 20 of FIG. 2 are not specifically shown in FIG. 4, it will be understood that the components 36 of FIG. 4 are intended to be co-located in a primary slab such as the slab 11 of FIG. 2 (or possibly more than one of such slabs), which in turn is mounted in between a pair of additional slabs corresponding to the slabs 18, 20 of FIG. 2. Also, it will be understood that the components 36 (along with slabs) can be formed on a single chip in at least some embodiments. As shown, the components 36 include a microfluidic channel 38 that is a single channel proximate to the mid-range of the system but branches off into first and second sets of three channels 40 and 42 at opposite ends. Respective ends 44 of the sets of channels 40, 42 are coupled to tap points 46, which are representative of locations on a chip at which it is possible for the chip to be coupled to fluid sources/reservoirs/receptacles.

Further as shown in FIG. 4, the components 36 include first, second, third, fourth, fifth and sixth waveguides 50, 52, 54, 56, 58, and 60. The first through third waveguides 50-54 extend inward toward the microfluidic channel 38 from a first structure 48 while the fourth, fifth and six waveguides 56-60 extend inward toward the microfluidic channel from a second structure 49. The structures 48, 49 can be considered to represent structures that allow for interaction with the respective waveguides 50-60. In at least some embodiments, the structures can represent interfacing with fiber optics to couple light into and out of the device. In other embodiments, the structures 48, 49 can represent light sources (e.g., a laser) and/or light sensors for providing light to or receiving light from the various waveguides. In further embodiments the structures 48, 49 can further represent one or more control devices that govern the supplying of light to one or more of the waveguides and/or monitor received light and/or take actions in response to the received light.

In the present embodiment, the first waveguide 50 in particular is intended to be a light source waveguide by which a light source (e.g., a light source forming part of the structure 48) directs light toward the microfluidic channel 38. Upon reaching the microfluidic channel 38 as incident light, the light that interacts with cells, particles or other material flowing through the microfluidic channel and results in scattered or fluoresced light that can be received by each of the other waveguides 52, 54, 56, 58, and 60. The light received in the waveguides 52-60 in turn is conveyed by those waveguides to light sensors (e.g., light sensors forming parts of the structures 48 and 49). The light that is sensed can include both scattered light and fluorescent light. More particularly as shown, the first waveguide 50 supplies light to the microfluidic channel 38 by way of a first pair of lenses 70, which in turn collimate and then focus the light toward a focal point (or region) 62 along the microfluidic channel 38.

Upon reaching the focal point 62 and interacting with the cells, particles or other material located there, light can scatter in a variety of directions. Each of the second through sixth waveguides 52-60 is orientated at a different respective angular orientation relative to an axis 63 extending between the focal point 62 and the first waveguide 50, such that the different waveguides 52-60 are respectively able to receive light emanating from the focal point along those different respective angular directions. Further as shown, second, third, fourth, fifth, and sixth pairs of lenses 72, 74, 76, 78, and 80 are respectively orientated between the focal point 62 and each of the respective waveguides 52, 54, 56, 58, and 60 such that the light emanating from the focal point in the various directions toward the various waveguides is focused by the respective lenses so as to enter those waveguides. The pairs of lenses 72-80 as well as the first pair of lenses 70 more particularly can be understood to include two lenses such as the lens 8 of FIG. 1 albeit, in other embodiments, the pairs of lenses can respectively be replaced with a single respective lens (or alternatively by more than two lenses).

In the present embodiment, the second and third waveguides 52 and 54, and their respective lens pairs 72 and 74, respectively, are orientated at approximately +15 degrees and −15 degrees relative to the axis 63 formed by the focal point 62 and the first waveguide 50. In contrast, the fifth waveguide 58 and its associated lens pair 78 are orientated directly opposite the first waveguide 50 and its lens pair 70, that is, on the opposite side of the microfluidic channel 38, such that light scattered or fluoresced in a direction diametrically opposite to the direction that incident light emanates towards the focal point 62 is what arrives at the waveguide 58. Additionally, the fourth and sixth waveguides 56 and 60 and their respective pairs of lenses 76 and 80, respectively, are oriented so as to receive light emanating at 20 degree intervals on either side of the axis 63 extending between the waveguide 58 and the focal point 62. As shown, the lens pairs 70-74 and 76-80 are all coupled to respective terminals 64 on the chip to allow for the providing or removal of fluid or other material to or from the various lens pairs. Likewise, the waveguides 50-54 and 56-60 respectively are coupled to respective terminals 66 that can (in at least some embodiments) allow for the providing or removal of fluid or other material to or from those waveguides.

The embodiment of FIG. 4 is intended to be representative of components of one exemplary microfluidic flow cytometer that employs multiple waveguides and multiple microfluidic lenses in addition to a microfluidic channel. Given the presence of the multiple waveguides and lenses arranged at different angles relative to the focal point 62, and further due to the presence of the slabs (not shown in FIG. 4 but shown in FIG. 2), scattered light emanating at a variety of directions can be captured and sensed, as can fluorescent light. Notwithstanding the above-described discussion, it should also be understood that many other embodiments are also possible and encompassed within the present invention. For example, in some alternate embodiments, the waveguides 50-60 can be replaced with optical fibers or even operate in combination with such devices. Also, the number of waveguides and lenses and orientations of those waveguides and lenses can vary depending upon the embodiment.

Further, in at least some embodiments (not shown) opaque/absorbing regions can be positioned so as to act as apertures, stops, or beam stops. For example, such absorbing regions can be positioned in front of or along the sides of a given lens so that the lens is restricted in terms of the light reaching it. Also, in at least some embodiments (not shown), waveguides can be formed by creating cladding regions, filled with a fluid or material of lower refractive index relative to that of the region of light travel, rather than creating and filling a core region. Additionally, in at least some embodiments, the curvature of the lens(es) can be made such that the relationship between the refractive indices of the light travel region and the lens(es) can be reversed. Also, in at least some embodiments, the outer surfaces of the lenses, microfluidic channels and/or waveguides need not be made from PDMS, but rather a variety of materials can be utilized. Further, lenses with non-spherical surface curvatures (two-dimensional aspheric or parabolic lenses) or other shapes can be used. Additionally, in at least some alternate embodiments, the lenses, channels and/or waveguides can be implemented on chips that employ non-channel perpendicular lamination, chips with more or less lenses or detection lines/waveguides, or chips with a channel having a curved interrogation region.

Figure 5:
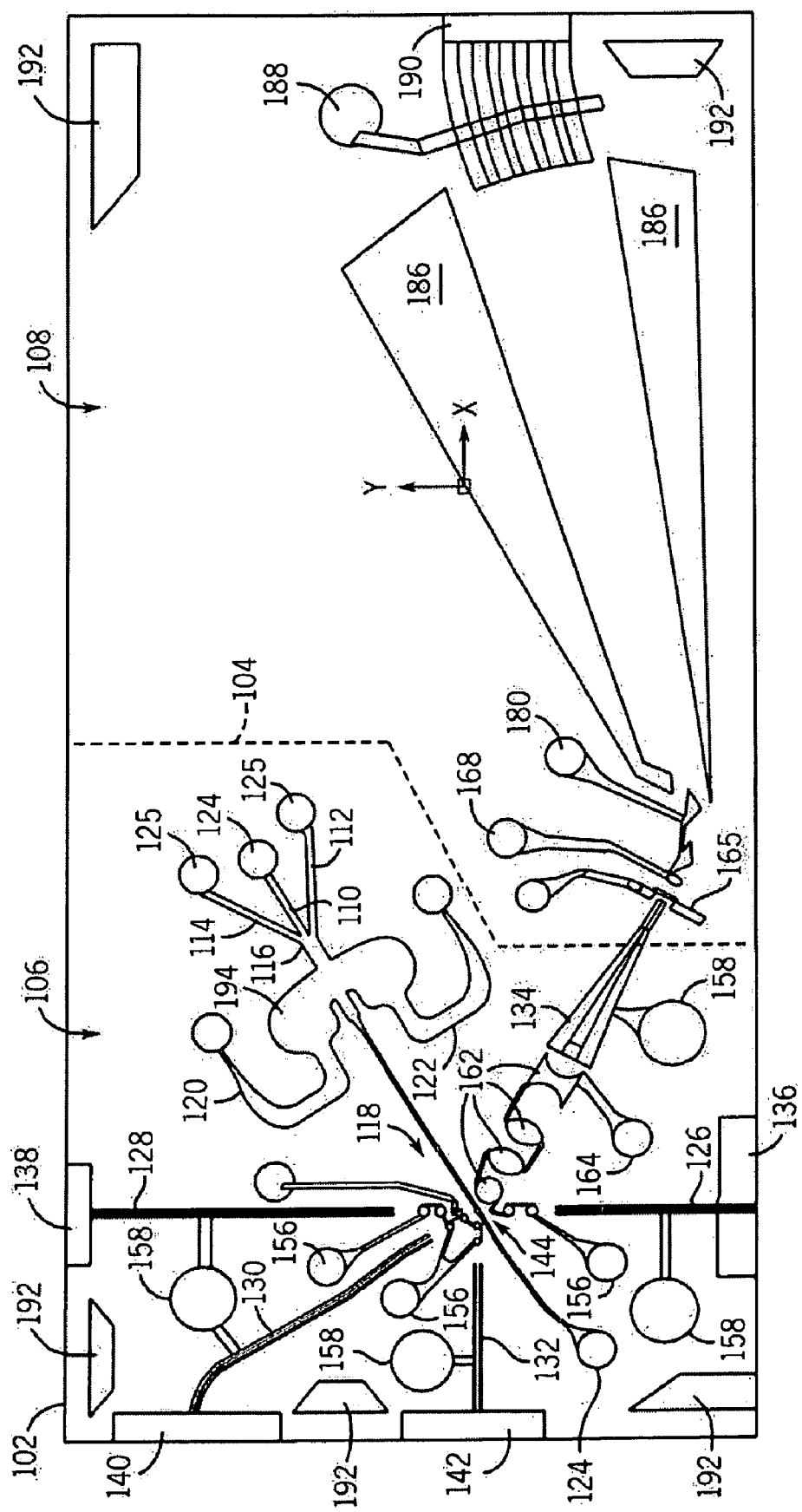
FIG. 5 is a top plan view showing, in schematic form, components of an exemplary microfluidic flow cytometer forming an interrogation region and a dispersion region of a single chip.

Turning now to FIG. 5, a top plan view of exemplary components of an additional flow cytometer located on a single microfluidic flow cytometry chip 102, in accordance with an additional embodiment of the present invention, is provided. As shown, the chip 102 is divided into two regions represented on either sides of a dashed line 104. The region on the left side of the dashed line 104 is an interrogation region 106, which employs components similar to those of FIGS. 1-4 arranged around a microfluidic channel for sampling a fluid flowing through the channel. Portions of the interrogation region 106 are shown in greater detail in FIG. 6 (in cutaway), as described below. The region on the right side of the line 104 is a dispersion region 108 employing, among other components, specialized optical components for collecting and observing emitted light emanating from the microfluidic channel. Additionally, portions of the dispersion region 108 are described in further detail in relation to FIG. 7 (again showing portions of this region in cutaway) and FIG. 8.

Although not shown in FIG. 5, it should be understood that, in at least some embodiments, the components of the respective interrogation and dispersion regions 106 and 108 can be co-located in a primary slab, such as the slab 11 of FIG. 2 or possibly on multiple such slabs. The primary slab (or multiple such slabs) can additionally be mounted in between two additional slabs (such as the additional slabs 18 and 20 of FIG. 2) to form a sandwich-like structure as described above. Notwithstanding the particular arrangement of the interrogation and dispersion regions 106 and 108, respectively, on the chip 102, other arrangements are possible depending upon the embodiment. In addition, although all the components of the flow cytometer are co-located on a single chip in the present embodiment, this need not always be the case. Rather, in other embodiments, entire regions or alternatively portions of one or both of the interrogation and the dispersion regions can be located on separate chips.

Figure 6:
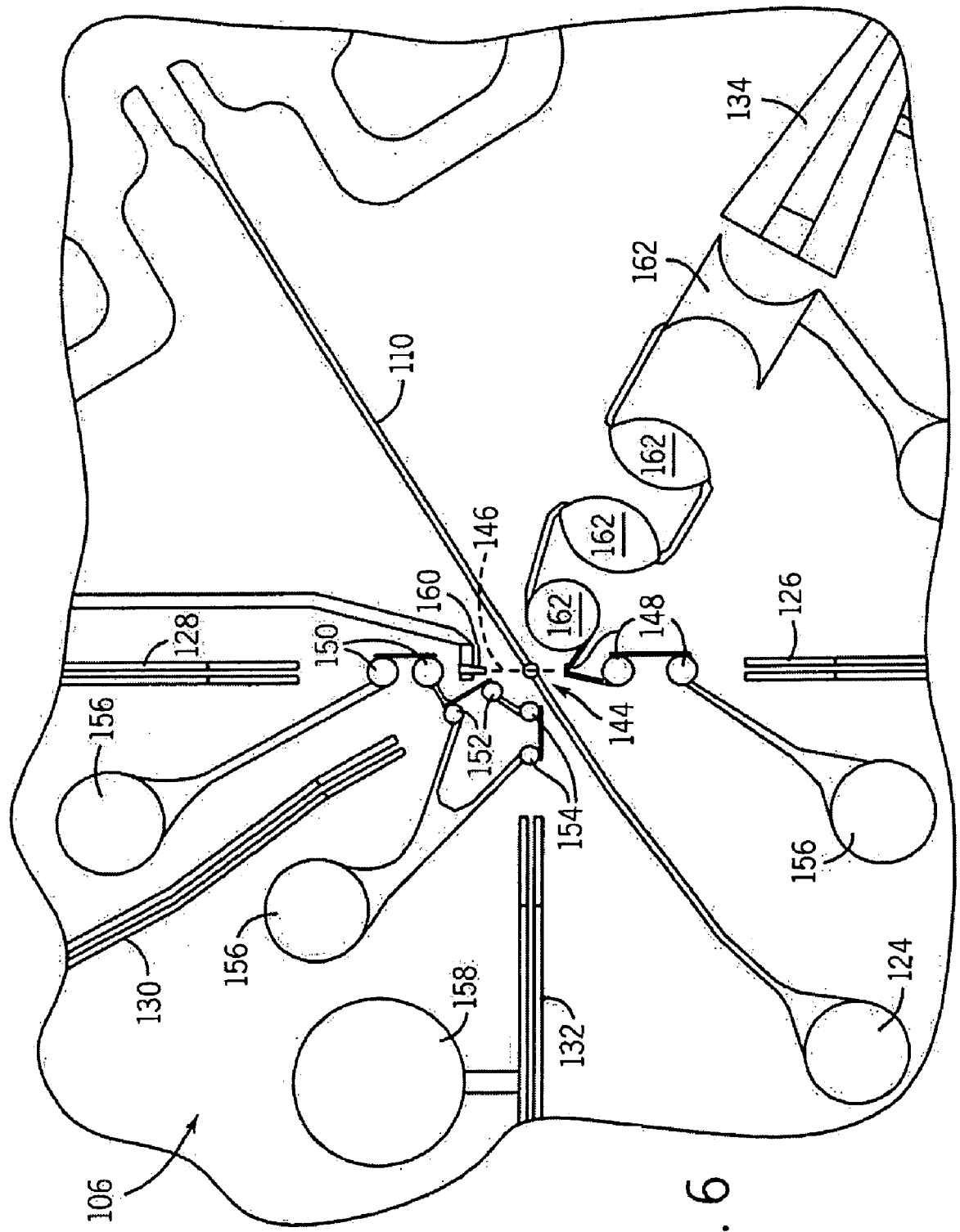
FIG. 6 shows in further detail (and in cutaway) a top plan view of portions of the interrogation region of the chip of FIG. 5.

Referring to FIG. 6 in addition to FIG. 5, the interrogation region 106 includes a microfluidic channel 110 for conducting sample fluids that can contain any of a variety of biological materials such as, for example, blood cells and other types of cells, particles and possibly other types of materials. The microfluidic channel 110 extends between tap points 124 located at opposite ends of the channel. Also provided on both sides of the channel 110 are first and second additional microfluidic channels 112 and 114 that extend from respective additional tap points 125 toward the microfluidic channel 110 and eventually merge with the microfluidic channel at a location 116.

The additional microfluidic channels 112, 114 serve as tributaries to the microfluidic channel 110 and, more particularly, serve to conduct clean fluid (e.g., fluid with no biological, particulate or other material) therethrough from the additional tap points 125 to the microfluidic channel 110. As it is introduced to the microfluidic channel 110 at the location 116, the clean fluid from the additional microfluidic channels 112 and 114 tends to surround the sample fluid conducted by the microfluidic channel 110. That is, the clean fluid tends to congregate along the walls of the microfluidic channel 110 and experience "sheath flow" while the sample fluid tends to flow within the middle of that microfluidic channel. Although in the present embodiment only the two additional microfluidic channels 112, 114 conducting clean fluid are shown, in other embodiments, a single channel or potentially more than two channels can be employed for this purpose as well.

The combined fluid (clean fluid plus the sample fluid) continues to proceed through the microfluidic channel 110 from the location 116 in a direction represented by an arrow 118 toward the tap point 124 at the far end of that microfluidic channel (although the combined fluid can be directed in other directions as well depending upon the embodiment). As will be described further below, effective illumination of the cells/particles/material within the sample fluid is enhanced by keeping the sample fluid in the center of the microfluidic channel 110. The presence of the clean fluid experiencing sheath flow around the sample fluid helps to maintain this condition. The tap points 124, 125 at the various ends of the microfluidic channels 110-114 are representative of locations on the chip 102 at which the chip can be coupled to fluid sources/reservoirs/receptacles for introducing the sample/clean fluids to, and/or removing those fluids from, the respective channels.

In addition to the aforementioned components, the interrogation region 106 of the chip 102 also includes a re-packing system 194 (see FIG. 5) that further improves the condition of the sample fluid, and particularly the condition of the cells/particles/material of interest within the sample fluid, for observation. More particularly, the re-packing system 194 serves to channel the flow of cells/particles/material of interest of the sample fluid in a narrow continuous stream within the microfluidic channel 110, in a manner such that the cells/particles/material of interest are spaced more compactly along the length of the microfluidic channel 110 and such that the cells/particles/material of interest move more slowly down that microfluidic channel. That is, the re-packing system 194 concentrates the sample to reduce 'dead' time in the device to improve throughput without the need for pre-concentrating steps, and reduces analyte travel speed as it passes farther down the microfluidic channel 110, allowing longer dwell times for more sensitive detection or the use of less sensitive detectors. In addition, the re-packing system 194 also allows for removal of excess clean (sheath) fluid from the additional microfluidic channels 112, 114, to prevent in-plane optical systems from needing to cope with large amounts of excess fluid. All of these impacts of the re-packing system 194 in turn improve the efficiency of sampling the sample fluid (or cells/particles/materials contained therein), particularly as observed at an interrogation point (or location or region) 144 along the microfluidic channel 110, as described further below with regards to FIGS. 9 and 10.

Figure 9:
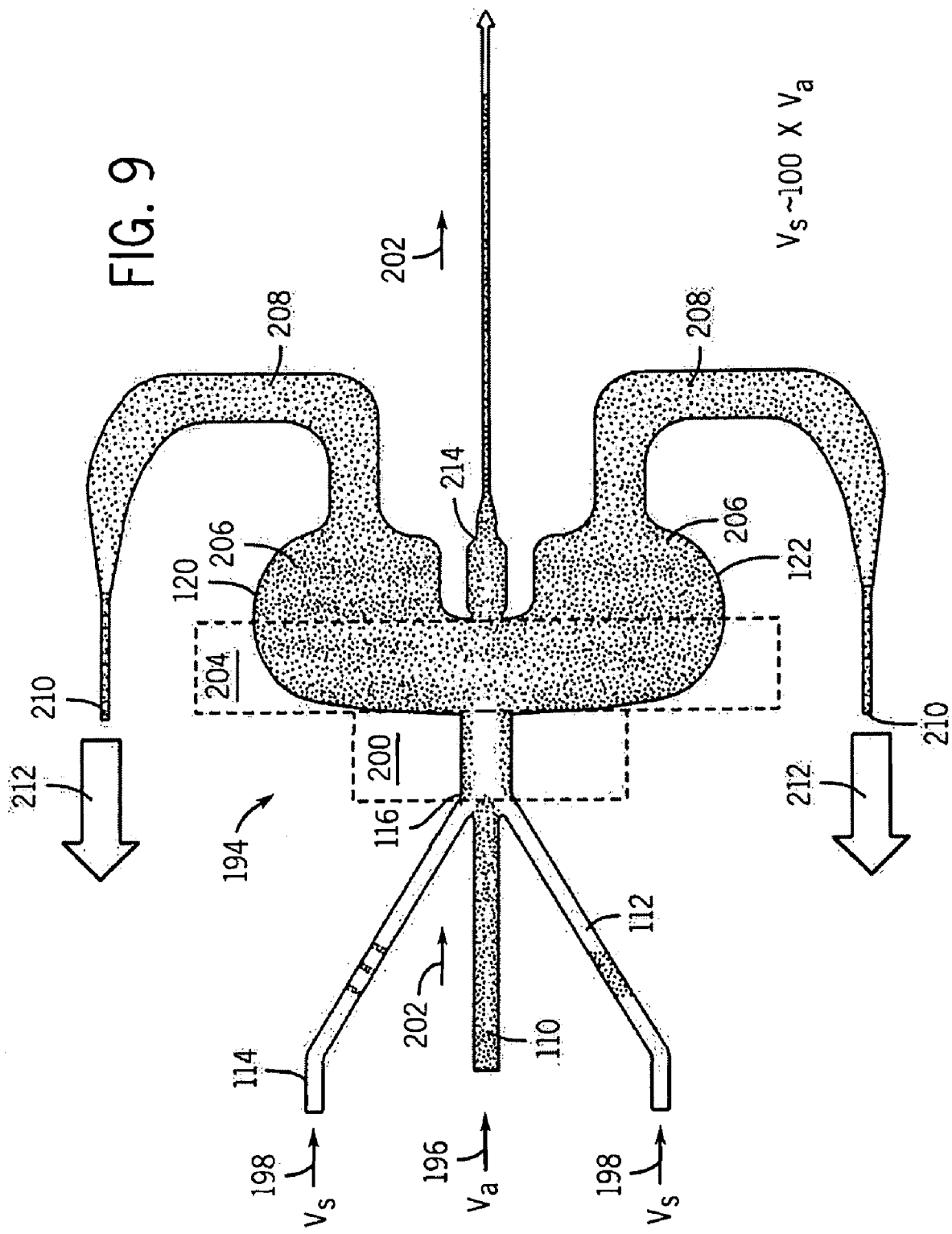
FIG. 9 shows, in schematic form, portions of the interrogation region of the chip of FIG. 5, including portions of an exemplary re-packing system.
Figure 10:
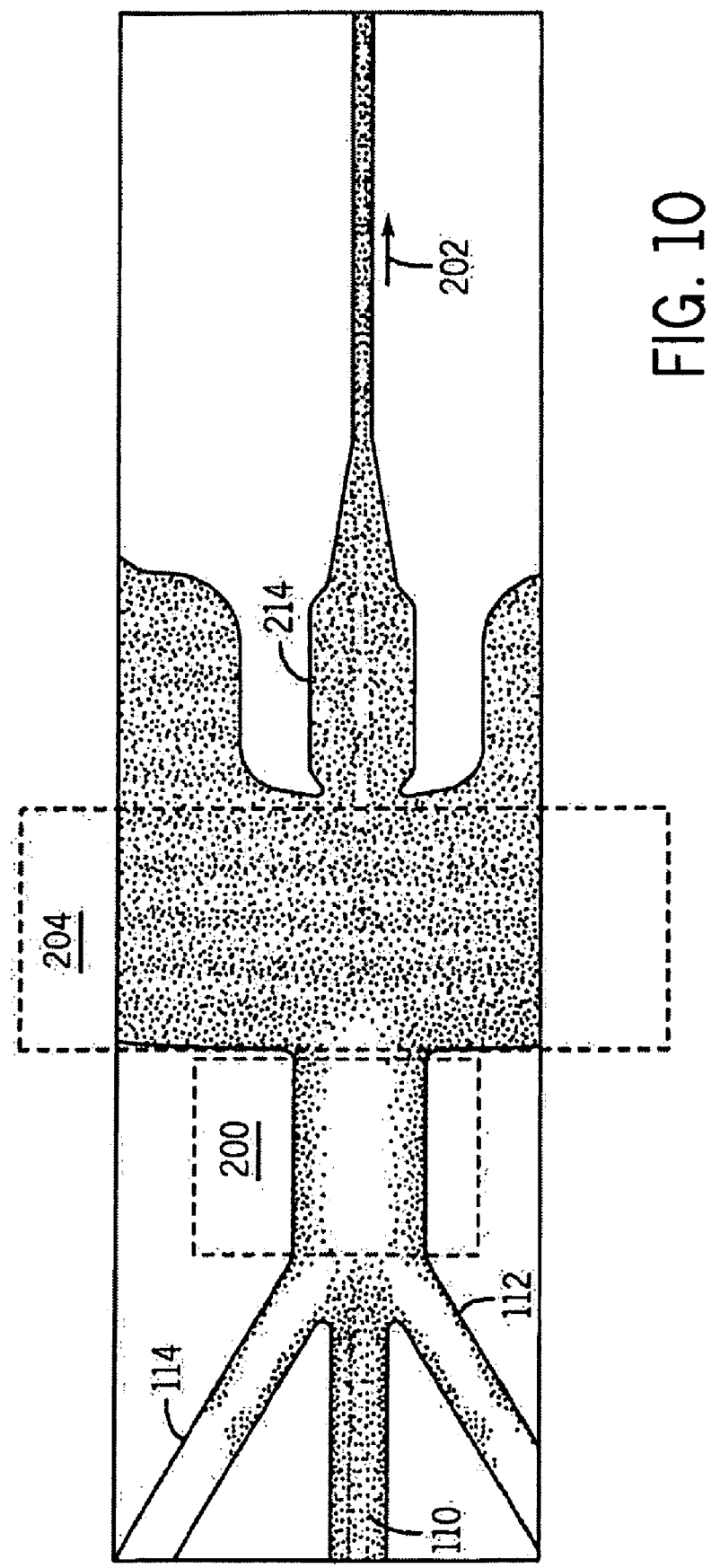
FIG. 10 shows, in cut-away, portions of the interrogation region including portions of the re-packing system of FIG. 9 in greater detail.

Referring to FIGS. 9-10, which respectively show portions of the interrogation region 106 and particularly the re-packing system 194 in further detail (in cutaway), the re-packing system operates as follows. The sample fluid containing cells/particles/material to be analyzed proceeds down the microfluidic channel 110 toward the re-packing system 194 in a direction represented by an arrow 196 with a velocity $V_a$. Additionally, clean fluid proceeds down the additional microfluidic channels 112, 114 toward the microfluidic channel 110 and particularly the location 116 along directions represented by arrows 198, with a velocity $V_s$ (or potentially two different velocities). Upon entering the microfluidic channel 110 at the location 116, the clean fluid experiences sheath flow (again at the velocity $V_s$) around the sample fluid already proceeding down that channel. In one embodiment of the present invention, the velocity $V_s$ of the sheath flow is approximately 100 times the flow rate of the sample fluid. In other embodiments, the flow rate of the sheath flow can be faster than the flow rate of the sample fluid by varying proportions.

Upon entering the microfluidic channel 110 at the location 116, the clean fluid to some extent confines the sample fluid. Due to the introduction of the clean fluid, "focusing" of the sample fluid flow occurs particularly at a first portion 200 of the microfluidic channel 110, that is, the sample fluid is concentrated at the center of the channel. According to Bang et al. (Bang, H., H. Yun, et al. (2006), "Expansion channel for microchip flow cytometers." Lab on a Chip 6(10): 1381-1383), which is hereby incorporated by reference herein, over-focusing (the high sheath to sample flow ratio) should bring the center of mass of the particles in the sample flow (e.g. cells,) close to the center of the focused sample flow stream.

Downstream of the first portion 200 of the microfluidic channel 110 is another, second portion 204 of the microfluidic channel, which can be considered also as constituting part of the re-packing system 194. As shown, the second portion 204 transitions in terms of its width rapidly from the width of the first portion 200 to a much wider width. Due to the much wider width of the second portion 204 (particularly at its maximum extent), both the sheath flow of the clean fluid and the flow of the sample fluid expand in width, which reduces the flow rate of the cells/particles/material of interest within the sample fluid (since the flow rate must be preserved). The slowing of the flow has the effect of concentrating the particles in the sample. At the same time, notwithstanding the decrease in the velocity of the cells/particles/material of interest, the cells/particles/material of interest within the sample fluid continue to flow down (and within) the channel 110 without being substantially disturbed (e.g., the flow of the cells/particles/material in an original direction represented by the arrow 202 is maintained). Insofar as the velocity of the cells/particles/material of interest decreases without flow disturbance, the cells/particles/material remain along the centerline (central axis) of the channel 110 as a result of the over-focusing of the flow that occurred in portion 200.

Already at the second portion 204, the speed of the sample fluid is slow, in contrast to the flow rate in the first portion 200. This slow speed of the sample travel is desirable for light scatter or fluorescence detection (e.g., to increase integration time). In addition, the cells/particles/material of interest of sample fluid are concentrated so as to minimize 'dead' time in the chip 102 without having to input a pre-concentrated sample into the device. Notwithstanding the beneficial focusing of the sample fluid within the channel 110, at the second portion 204 of the microfluidic channel 110 there is a great width of sheath fluid that will make in-plane interrogation or light collection difficult. That is, excess fluid surrounding the cells/particles/material of interest within the sample fluid can potentially make sampling difficult downstream at the interrogation point 144.

To improve sampling at the interrogation point 144, excess fluids surrounding the cells/particles/material of interest are removed from the microfluidic channel 110 following (downstream of) the second portion 204. As shown, the excess fluids are drained from the microfluidic channel 110 by the re-packing system 194 due to additional side channels 120 and 122 that are respectively connected to, and downstream of, the second portion 204 on opposite sides of the centrally-positioned microfluidic channel 110. More particularly, each of the side channels 120 and 122 is an outflow channel having a first expanded portion 206 and a second narrow portion 208 that leads to a respective outflow point 210 (e.g., a tap point similar to the tap points 124 discussed above). Thus, excess clean sheath fluid is drained from the microfluidic channel via the side channels 120, 122 of the re-packing system 194.

Notwithstanding the draining action that occurs due to the side channels 120 and 122, and due in part to over-focusing, the overall shift in the center of mass of the cells/particle/material of interest within the sample fluid is minimized. Also, insofar as the disturbance is minimized, the cells/particles/material of interest continue to travel roughly along the centerline of the microfluidic channel 110 in the direction of the arrows 202 towards the interrogation point 144. Upon passing through the second portion 204, aside from the clean fluid that is drained by the side channels 120, 122, most of the sample fluid including the focused cells/particles/material of interest and some of the clean fluid experiencing sheath flow enters a third portion 214 of the microfluidic channel 110 (which can be, but need not be, considered as constituting part of the re-packing system 194), subsequent to which the width of the channel 110 is significantly reduced, as explained below.

The dimensions of the third portion 214 (in addition to the design of the side channels 120, 122) serve to minimize any increase in fluid velocity while maintaining the focused flow of cells/particles/material of interest therethrough. In one embodiment, the width of the channel 110 is reduced on a scale of tens of microns as compared to the width of the channel before the first portion 200 (although the reduction can vary depending upon the embodiment). By virtue of the flow expansion in the second portion 204 followed by excess fluid removal through both the side channels 120 and 122, the flow velocity of the sample fluid containing the streamlined cells/particles in the channel 110 after the third portion 214 is reduced by approximately 5 times as compared to the initial flow before the re-packing system 194, in the first portion 200.

The re-packing system 194, and particularly the structure and design of the channels 120 and 122, afford several advantages, particularly in terms of focusing the sample fluid (and particularly the cells/particles/material of interest) for providing efficient sampling. By reducing the amount of fluid traveling within the microfluidic channel 110 (and surrounding the sample fluid with the clean fluid within the channel 110), the travel speed of the sample fluid as it passes the interrogation point 144 is reduced, thus increasing the dwell time of the sample fluid at the interrogation point and enabling sensitive and efficient detection of the cells/particles/material of interest within the sample fluid. Increasing the dwell time at the interrogation point 144 also provides an additional benefit where less sensitive (and therefore, less expensive) detectors can be employed within the chip 102, thereby reducing the overall cost of the chip. Additionally, employing the side channels 120 and 122, respectively, to remove the excess sheath fluid within the microfluidic channel 110 concentrates the sample substantially in the center of the channel 110 to reduce "dead" time within the chip 102. By virtue of reducing the "dead" time, the throughput (e.g., the number of cells that can be interrogated in a given period of time) is significantly improved while eliminating or substantially minimizing pre-concentrating of the sample fluid before entering the channel 110. Further, the removal of excess sheath fluid prevents in-plane optical systems from needing to cope with large amounts of excess fluid at the interrogation point 144.

In general, the microfluidic channels 112, 114, 120 and 122 have walls that are made of a material (or multiple materials) having a refractive index that is lower than the refractive index of the microfluidic channel 110. For example, in some embodiments, the channels 112-114 and 120-122 can be made of a lower index (e.g., n=1.41) polydimethylsiloxane (PDMS) optical elastomer as compared to the channel 110, which can be made of a higher index PDMS (e.g., n=1.42). In other embodiments, the channels 110-114 and 120-122 can be made of one or more materials other than those indicated above, with the channel 110 having a higher refractive index than the remaining channels.

Still referring to FIGS. 5 and 6, the interrogation region 106 additionally includes first, second, third, fourth and fifth waveguides 126, 128, 130, 132 and 134, respectively, surrounding the microfluidic channel 110 but spaced somewhat apart from that channel. As shown, each of the respective waveguides 126, 128, 130 and 132 extends inwardly, towards the interrogation point 144, from respective structures 136, 138, 140 and 142. In particular, similar to the structures 48 and 49 of FIG. 4, each of the structures 136-142 can be considered to represent one or more structures that allow for interaction with the respective waveguides 126-132. In at least some embodiments, the structures can represent interfacing with fiber optics to couple light into and out of the chip 102 or, alternatively, the structures can be light sources (e.g., a laser) and/or light sensors for providing light to or receiving light from the various waveguides. In further embodiments, the structures 136-142 can represent one or more control devices that govern the supplying of light to one or more of the waveguides and/or monitor received light and/or take actions in response to the received light. Although in some embodiments, a structure similar to the other structures 136-142 can be employed in relation to the fifth waveguide 134 (e.g., at its far end opposite the end proximate the point 144), as will be described below, in the present embodiment other structures are positioned at this end of the waveguide.

Further with respect to the waveguides 126-134, in the present embodiment the first waveguide 126 is particularly intended to be a light source for accomplishing illumination of the interrogation point 144 (which also can be considered a focal point) of the microfluidic channel 110. As shown, the first waveguide 126 (see FIG. 6) is positioned substantially along an axis 146 through the point 144, although the waveguide can be positioned in other directions as well depending upon the embodiment. By directing light from a light source (e.g., a solid state laser) of the structure 136 into the waveguide 126, the illumination beam exiting that waveguide can focus light towards the point 144 by way of a pair of illumination lenses 148. The illumination lenses 148 are generally positioned substantially along the axis 146 in between the first waveguide 126 and the point 144 and are similar to the pairs of lenses 72-80 of FIG. 4. Therefore, light from the first waveguide 126 is directed to the pair of lenses 148, which in turn shape and collimate the light beam towards the point 144 along the microfluidic channel 110. In particular, the pair of lenses 148 are shaped to collect light from the first waveguide 126 and collimate the light into a thin beam across the microfluidic channel 110.

As the sample fluid surrounded by clean fluid passes the point 144 within the microfluidic channel 110, the cells, particles or other material within the fluid interact with the light beam from the waveguide 126 resulting in scattered illumination light or even (depending upon the material of interest) fluorescent light that is emitted in various directions. Such scattered illumination or fluorescent light can be received by each of the other waveguides 128-134 depending upon the angle(s) of scattering/fluorescence and the orientations of the waveguides relative to the angle(s) of scattering/fluorescence. Typically, the second, third, fourth and the fifth waveguides 128, 130, 132 and 134, respectively, are oriented so as to extend along respective different angles with respect to the axis 146 such that light emanating from the point 144 in various directions can enter respective ones of the waveguides. Further as shown, each of the waveguides 128, 130, 132, and 134 has associated with it a respective pair of lenses positioned in between the point 144 and the respective waveguide such that light emanating from the point 144 in the direction of the respective waveguide is focused into the respective waveguide via the respective pair of lenses.

Various types of lenses are possible. In the present embodiment, for example, a pair of forward light scatter collection module lenses 150, which collect light over a smaller angular range (e.g., a smaller numerical aperture lens system), is positioned between the microfluidic channel 110 and the respective second waveguide 128, substantially along the axis 146 on the opposite side of the microfluidic channel 110 relative to the first waveguide 126, such that light scattered at small forward angles (e.g., <10 degrees relative to the axis) can be collected by that pair of lenses and directed into the second waveguide (which can be termed a forward scatter waveguide). Relatedly, light scattered at larger forward angles (e.g., approximately 15-30 degrees relative to the axis 146) is collected using a pair of small-angle light scatter module lenses 152 positioned between the microfluidic channel 110 and the third waveguide 130 (which can be termed a small angle light scatter collection waveguide). Similarly, light scattered around 90 degrees from the axis 146 (orthogonal scatter) can be collected by a pair of orthogonal scatter module lenses 154 positioned between the microfluidic channel 110 and the fourth waveguide 132 (which can be termed an orthogonal scatter collection waveguide).

Further as shown in FIGS. 5 and 6, each of the pairs of lenses 148-154 is coupled to respective terminal points 156 on the chip 102 for introducing into or removing fluids/other materials from the respective lenses. In this manner, characteristics of the lenses 148-154 can be varied by varying characteristics (or amounts) of the fluids forming those lenses (as contained within lens cavities of the chip 102). Likewise, each of the waveguides 126-134 can be coupled to terminal points 158 for introducing or removing fluids or other materials from the respective waveguides, thereby also allowing for adjustment of characteristics of the waveguides (albeit in some embodiments the waveguides are solid material waveguides or are merely empty cavities). Additionally, an opaque/absorbing region on the chip 102 serves as a beam stop 160 for blocking, at least in part, the illumination beam arriving from the first waveguide 126, so as to ensure that scattered (or fluorescent) light, rather than the illumination beam itself, is received and detected by way of the second waveguide 128, the associated lenses 150, and the structure 138. Further, although the respective pairs of lenses 148-154 are employed with each of the respective first, second, third and fourth waveguides 126-132, in other embodiments, a single lens or possibly more than two lenses can be employed with one or more of those waveguides.

As already indicated above, while in some embodiments the sample fluid upon being illuminated produces scattered light for receipt by the waveguides 128-134, in at least some embodiments the sample fluid is instead (or additionally) fluorescently labeled with an excitable tag such that the interaction of the sample fluid with the illumination light can result in the emission of fluorescent light. Similar to scattered light, fluorescent light can be collected for observance by multiple lenses, waveguides and detectors. Significantly, such emitted fluorescent light can also be separated by wavelength, thus allowing fluorescent light signals to be routed to/sensed by different detectors (or different elements of a detector array) for efficient monitoring of those signals. In the present embodiment, the separation of fluorescent light into various wavelengths is performed in the dispersion region 108 of the chip 102, as described in greater detail with respect to FIGS. 7 and 8.

As is further shown in FIGS. 5-6, in the present embodiment emitted fluorescent light can be collected by fluorescence module lenses 162 positioned between the point 144 and the fifth waveguide 134. The fluorescence module lenses 162 are similar to the aforementioned lenses 148-154 for collecting scattered illumination light from the sample fluid. As with the other lenses 148-154, the lenses 162 are coupled to a tap point 164 for introducing or removing fluids/other materials from the lenses, thereby again allowing for variations to be made to the characteristics of the lenses. In the present embodiment, the lenses 162 are positioned at approximately 45 degrees from the axis 146, although other angular orientations depending upon the angle of emitted fluorescent light are possible in other embodiments. The emitted fluorescent light from the sample fluid in particular is directed by way of the lenses 162 to enter the fifth waveguide 134, which in turn transmits the fluorescent light into the dispersion region 108 of the chip 102, described below.

Figure 7:
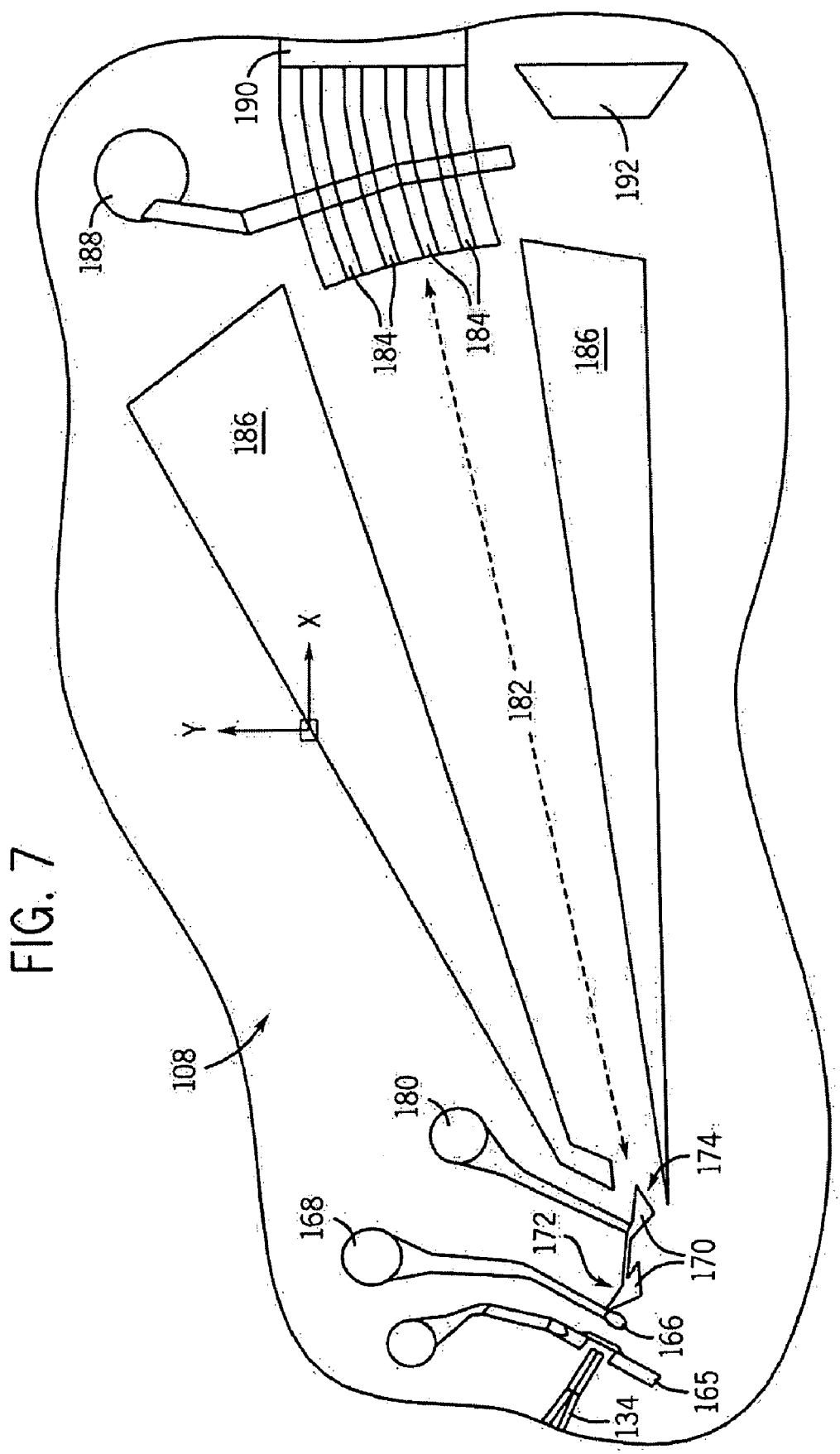
FIG. 7 shows in further detail (and in cutaway) a top plan view of portions of the dispersion region of the chip of FIG. 5.

Referring now to FIG. 7 (in conjunction with FIG. 5), portions of the dispersion region 108 of the chip 102 are shown in schematic form in further detail (in cutaway). As shown, the fluorescent light from the sample fluid directed via the lenses 162 into the fifth waveguide 134 is then further directed by that waveguide to enter and pass through an aperture 165 in the dispersion region 108. The light from the aperture 165 then enters another microfluidic lens 166 for collimating the fluorescence signal onto additional optical elements for separating the fluorescent light into different wavelengths. The lens 166 is similar in construction and design to the lenses 162 described above. In particular, the lens 166 is a fluid filled lens connected to a tap point 168 through which fluid or other materials can be introduced to or removed from the lens so as to vary its lens characteristics. The light from the lens 168 in particular is directed toward and incident upon a wavelength separating system that, in the present embodiment, is a prism system 170 including a pair of first and second prisms 172 and 174, respectively, which are arranged proximate to each other as described below additionally in relation to FIG. 8.

Figure 8:
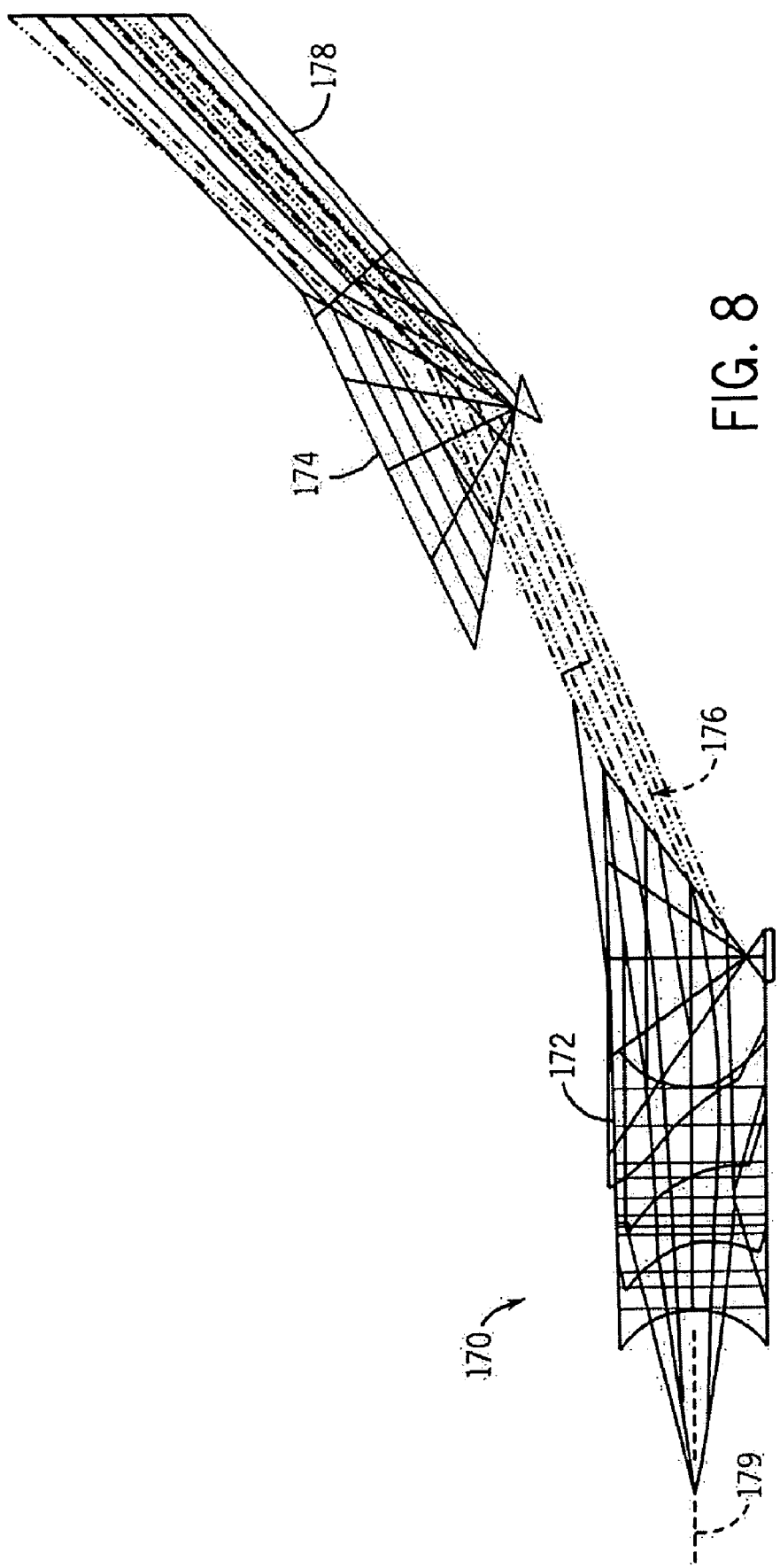
FIG. 8 shows in greater detail a top plan view of an exemplary wavelength separating system that can be employed in the dispersion region of the chip of FIG. 5.

Turning to FIG. 8, the prism system 170 is shown in schematic form. As indicated above, the fluorescent light from the fluid passes via the lenses 162, the fifth waveguide 134, the aperture 165 and the lens 166 toward the prism system 170, and in particular is directed first toward the first prism 172. As the fluorescent light travels through the first prism 172, the fluorescent light is separated into portions of light of various spectra 176 corresponding to different ranges of frequency/wavelength. These portions of light of various wavelengths from the first prism 172, upon exiting that prism, are then further incident upon the second prism 174, which as shown is positioned at an angle relative to the first prism. The second prism 174 in particular additionally disperses the various incoming portions of light of different spectra 176 and in turn outputs outgoing portions of light 178 at different angles relative to one another, so as to provide a greater physical separation of the outgoing portions of light. The angular arrangement and orientation of the prisms 172 and 174 can vary depending upon the embodiment based upon a variety of considerations including, for example, the required separation of the various wavelengths of the fluorescent signals.

Particularly, light exiting from each of the prisms 172 and 174 emerges traveling at an angular offset from an optical axis 179 of the incoming light (beam steering). For different wavelengths of light, the angular offset is different. In at least some embodiments, the prisms 172 and 174 are chosen to have a large apex for maximizing prism width (light path length inside the prism) although prisms having a smaller apex can be used in alternate embodiments. For example, in the present embodiment, each of the prisms 172 and 174 has a prism apex of 110 degrees, and the second prism 174 is rotated 25 degrees from the optical axis 179 to follow the light path as it emerges from the first prism 172. In other embodiments, the prisms 172 and 174 can have prism apices and degrees of rotation that are different from those mentioned above. Specifically, the orientation of the prisms 172 and 174 with respect to the optical axis is determined by the need to prevent reflection of light such that the angle of light incidence is below the critical angle for total internal reflection, to enable light to transmit through the prism.

With respect to the prisms 172 and 174 in particular, both of the prisms in the present embodiment are microfluidic prisms connected to a tap point 180 for introducing or removing fluids or other materials from the prisms, as shown in FIG. 7. In general, the prisms are filled with an optical fluid (or other material) similar to that used to fill the various lenses 148-

154, 162 and 166 employed in the chip 102. As fluid-filled microfluidic prisms, the prisms 172 and 174 serve as chromatically dispersive elements (operating according to Snell's Law) for separating the spectra of the fluorescent light signals, allowing for detection of various cells/particles/other materials without the use of any dichroics or optical filters. Use of the prisms allows one to avoid splitting or partially absorbing an already weak signal. Additionally, in at least some embodiments, it allows the signals to be monitored by detectors that do not discriminate wavelength (e.g., less expensive and faster detectors).

Nevertheless, in alternate embodiments, the prisms 172 and 174 can be used in conjunction with one or more other optical elements including various dichroics and optical filters for separating the fluorescent light signals by wavelength. Additionally, in at least some embodiments, the prisms 172 and 174 can be made out of channels having flat walls intersecting at particular angles to form light dispersive elements for separating light by wavelength. Also, in at least some alternate embodiments, one or more of the prisms are not microfluidic prisms containing liquid, but rather are solid prisms. In further embodiments, only one prism or more than two prisms are employed as the prism system 170 rather than two prisms.

Indeed, in at least some embodiments of the present invention, it is envisioned that one or more of the prisms, lenses, waveguides or other structures will be solid structures. In some such embodiments, the solid structures will be cavities that are formed by filling up a cavity with fluid and then turning that fluid into a solid (or semi-solid) material by a process such as thermal or ultra-violet curing.

Referring to FIGS. 7 and 8, upon exiting the second prism 174, the separated outgoing portions of light 178 travel a propagation distance within a propagation region 182 to further broaden the physical width of the different spectra as well as to increase the distances between the different spectra. This allows the different spectra to be directed respectively to a plurality of different waveguides 184. The propagation region 182 within which the light travels is typically flanked by large apertures 186 on both sides to prevent stray light from entering the chip 102. The apertures 186 are typically filled with an opaque black PDMS (e.g., Sylgard 170) for blocking light passing through the apertures. In other embodiments, the apertures 186 can be filled with other types of materials as well that are suitable for blocking light. The waveguides 184 are positioned at the end of the propagation distance 182 with each waveguide being configured to collect a respective known 'passband' (a respective one of the wavelength spectra of the light 178 of the fluorescence signals) of light determined by the physical width of the spectrum at the point of incidence with the waveguides.

In the present embodiment, the waveguides 184 are made up of a plurality of waveguides connected in an array with each waveguide in the array being capable of receiving a particular wavelength of light from the separated outgoing portions of light 178. Additionally, as shown, the waveguides 184 are coupled to a tap point 188 for introducing and/or removing fluid from within the waveguides. Further, similar to the waveguides 126-132, the waveguides 184 can be coupled to a structure (or multiple structures) 190 for interacting with the waveguides 184. In at least some embodiments, the structure 190 can be a detector (or array of detectors) for receiving portions of light of various wavelengths from the waveguides 184 for allowing for separate detection of light intensities from each passband. In at least some alternate embodiments the various passbands of light can be detected directly by the detectors without interfacing with the waveguides 184. By virtue of separating light by wavelength, the fluorescent light signals emanating from the point 144 thus can be routed to different detectors (or different elements of an array detector), and can thereby avoid splitting or partial absorbing of weak signals.

The above-described embodiments encompassing lens components, waveguides (or optical fibers), prisms and microfluidic channels located on the chip lend themselves to a relatively easy process of manufacturing in which the various components are created in a primary or core slab and then the two additional or cladding slabs are positioned above and below the core slab. Thus, single-chip systems can be readily developed, which depending upon the embodiment can be manufactured using a variety of processes (e.g., injection molding, laser cutting and other methodologies). Further, in some embodiments, each lens structure can be micro-fabricated (so that it is smooth), albeit other techniques can also be employed to manufacture such lenses. It should be evident that optical surface quality is an important characteristic, particularly when forming the lens components and prisms (albeit it can be significant for other structures as well, such as waveguides). Indeed, in further embodiments, three dimensional lenses can be fabricated in chips where the lenses are filled with a high index fluid or polymer or other such material. In at least some embodiments, additional structures, such as structures 192 (see FIGS. 5 and 7) can be employed as simple place-markers for cutting out individual devices/chips (e.g., cut lines).

Further, in at least some embodiments (not shown), waveguides can be formed by creating cladding regions, filled with a fluid or material of lower refractive index relative to that of the region of light travel, rather than creating and filling a core region. Additionally, in at least some embodiments, the curvature of the lens(es) can be made such that the relationship between the refractive indices of the light travel region and the lens(es) can be reversed. Also, in at least some embodiments, the outer surfaces of the lenses, microfluidic channels and/or waveguides need not be made from PDMS, but rather any of a variety of other materials can instead (or additionally) be utilized. Further, lenses with nonspherical surface curvatures (e.g., two-dimensional aspheric or parabolic lenses) or other shapes can be used. Additionally, in at least some alternate embodiments, the lenses, channels and/or waveguides can be implemented on chips that employ non-channel perpendicular lamination, chips with more or less lenses or detection lines/waveguides, or chips with a channel having a curved interrogation region. Although the above-described embodiments envision fabrication of devices including microfluidic channels (including possibly more than one such microfluidic channel on a given chip), waveguides, lenses, and prisms (and possibly other circuitry) on single chips, the present invention can also encompass embodiments in which such structures are formed and/or combined in other manners.

A significant application of at least some embodiments of the present invention is an on-chip, micro-flow cytometer with incorporated optics, having primary application to immunology and cancer research, as well as for routine clinical diagnostic applications, such as HIV (AIDS) diagnosis and therapy monitoring. The system can be employed in flow cytometry and general immunofluorescence to create a more compact, integrated, and likely lower-cost device that requires fewer or no dichroics or optical filters. Other applications for the on-chip separation of light in such a manner can be envisioned. In at least some embodiments, it is possible that devices similar to those described above can be integrated with other developing technologies, including technologies for on-chip cell sorting and microfluidic hydrodynamic focusing.

Further, it should be understood that, depending upon the embodiment of the present invention, liquid and air can both be considered as "fluid" and our device concept is applicable to detection of both liquid suspended objects and aerosols. Also, at least some embodiments of the present invention are intended to allow for mass-production/fabrication of many micro-flow cytometer chips; for example, one can potentially fill in many (even thousands of) lenses, prisms, and/or other structures with fluid at a given time and then subsequently cure the fluid (again via thermal or ultraviolet curing, for example) to cause it to become solid within each of those chip structures simultaneously (it will be understood that, by initially using fluids to fill up the lenses/prisms/other structures, it is easier to fill up those structures entirely, regardless of their internal shapes).

Further, in at least some embodiments it is possible for the lens (or prism or possibly some other structure) media to be altered in a controllable manner to make the lens into a tunable lens. For example, the lens chamber can be filled up with liquid crystal. With an applied electric field, the index of refraction of the liquid crystal can be changed, yielding a lens with tunable focal distance. Or the lens medium can contain suspended nanoparticles. The concentration of the nanoparticles can be controlled by thermal gradient, electric field, or magnetic field (e.g. magnetic nanoparticles). With tunable lenses integrated with waveguides and microfluidic channels, one can scan and steer the beam and perform other functions to assist light detection.

Additionally, embodiments of the present invention are also intended to be applicable to other applications in addition to or instead of flow cytometry systems and methods. Further, it should be further understood that, to the extent that any particular discussion is provided above in relation to any particular one or more of the embodiments of the invention in terms of possible modifications, advantages, and/or applications thereof, it is intended that such discussion should be understood as pertaining to all of the embodiments herein.

It is specifically intended that the present invention not be limited to the embodiments and illustrations contained herein, but include modified forms of those embodiments including portions of the embodiments and combinations of elements of different embodiments as come within the scope of the following claims.

We claim:

1. A system for flow cytometry, the system comprising:
   a microfluidic channel;
   a first light conveying structure having first and second ends, wherein the first end is arranged proximate to the microfluidic channel; and
   at least one microfluidic prism arranged proximate to the second end of the first light conveying structure,
   wherein light emanating from the microfluidic channel is provided to the first light conveying structure at the first end, conveyed by way of the first light conveying structure to the second end, and in turn provided to the at least one microfluidic prism,
   wherein the at least one microfluidic prism in turn outputs a plurality of portions of the light at a plurality of different frequency ranges, respectively, in a plurality of different directions, respectively, and
   wherein at least one of the following is true:
   (a) the light emanating from the microfluidic channel includes scattered light;
   (b) the light emanating from the microfluidic channel includes fluorescent light; and
   (c) the light emanating from the microfluidic channel is indicative of light absorption that has occurred due to a presence of material within the microfluidic chamber.

2. The system of claim 1, wherein the at least one microfluidic prism includes first and second microfluidic prisms, wherein the light provided to the at least one microfluidic prism is incident on the first microfluidic prism, which in turn directs at least some of the light to the second microfluidic prism, which in turn outputs the plurality of portions of the light.

3. The system of claim 1, wherein the at least one microfluidic prism is coupled to a tap by which a selected fluid can be directed into or removed from the at least one microfluidic prism, whereby an optical characteristic of the microfluidic prism can be modified.

4. The system of claim 1, wherein the microfluidic channel receives a sample fluid from a first source and additionally receives an additional fluid from a second source.

5. The system of claim 4, wherein the additional fluid is directed into the microfluidic channel in such a manner so that the additional fluid is positioned within the microfluidic channel substantially around the sample fluid, the additional fluid experiencing sheath flow down the microfluidic channel.

6. The system of claim 4, further comprising a re-packing system having a re-packing passage leading between the microfluidic channel and an outlet, the re-packing passage serving to drain at least a portion of one or both of the sample fluid and the additional fluid, whereby an average spacing between particles within the sample fluid is reduced between a first location within the microfluidic channel upstream of the re-packing system and a second location within the microfluidic channel downstream of the re-packing system, and whereby an average speed of movement of the particles within the sample fluid is reduced between the first and second locations.

7. The system of claim 1, further comprising a first lens structure arranged between the microfluidic channel and the first end of the first light conveying structure, wherein at least one component of the system includes a wall made from polydimethylsiloxane (PDMS).

8. The system of claim 1, further comprising a first lens structure arranged between the microfluidic channel and the first end of the first light conveying structure, and additionally comprising a second lens structure arranged between the second end of the first light conveying structure and the at least one microfluidic prism, wherein each of the first and second lens structures is a respective fluidic lens having a respective outer wall and a respective internal fluid, wherein at least one of the first and second lens structures is connected to a tap by which the respective internal fluid can be driven into or removed from the respective lens structure, and wherein the first light conveying structure is selected from the group consisting of a waveguide and an optical fiber.

9. The system of claim 1, further comprising a plurality of light sensors arranged at a plurality of respective locations so as to receive respective ones of the portions of the light output by the at least one microfluidic prism in respective ones of the different directions, the respective ones of the portions of the light being at different respective frequencies.

10. The system of claim 1, wherein the system comprises at least one additional light conveying structure, wherein each of the at least one additional light conveying structure and the first light conveying structure is oriented so as to receive at least one of the light and additional light emanating from an interrogation region of the microfluidic channel.

11. The system of claim 10, wherein incident light is directed toward the interrogation region of the microfluidic channel by way of at least one further light conveying structure.

12. The system of claim 1, wherein the microfluidic channel, the first light conveying structure, and a lens structure positioned therebetween are all formed within an intermediate slab formation sandwiched between first and second slab formations.

13. The system of claim 1, wherein the microfluidic channel, the light conveying structure, the at least one microfluidic prism and a lens structure are all assembled on a single chip.

14. A system for flow cytometry, the system comprising:
a microfluidic channel, wherein the microfluidic channel receives a sample fluid from a first source and additionally receives an additional fluid from a second source;
a first light conveying structure having first and second ends, wherein the first end is arranged proximate to the microfluidic channel; and
at least one microfluidic prism is arranged proximate to the second end of the first light conveying structure; and
a re-packing system having a re-packing passage leading between the microfluidic channel and an outlet, the re-packing passage serving to drain at least a portion of one or both of the sample fluid and the additional fluid, whereby an average spacing between particles within the sample fluid is reduced between a first location within the microfluidic channel upstream of the re-packing system and a second location within the microfluidic channel downstream of the re-packing system, and whereby an average speed of movement of the particles within the sample fluid is reduced between the first and second locations,
wherein light emanating from the microfluidic channel is provided to the first light conveying structure at the first end, conveyed by way of the first light conveying structure to the second end, and in turn provided to the at least one microfluidic prism, and
wherein the at least one microfluidic prism in turn outputs a plurality of portions of the light at a plurality of different frequency ranges, respectively, in a plurality of different directions, respectively.

15. The system of claim 14, wherein the at least one microfluidic prism includes first and second microfluidic prisms, wherein the light provided to the at least one microfluidic prism is incident on the first microfluidic prism, which in turn directs at least some of the light to the second microfluidic prism, which in turn outputs the plurality of portions of the light.

16. The system of claim 14, wherein the at least one microfluidic prism is coupled to a tap by which a selected fluid can be directed into or removed from the at least one microfluidic prism, whereby an optical characteristic of the microfluidic prism can be modified.

17. The system of claim 14, wherein at least one of the following is true:

the light emanating from the microfluidic channel includes scattered light;
the light emanating from the microfluidic channel includes fluorescent light; and
the light emanating from the microfluidic channel is indicative of light absorption that has occurred due to a presence of material within the microfluidic chamber.

18. A system for flow cytometry, the system comprising:
a microfluidic channel;
a first light conveying structure having first and second ends, wherein the first end is arranged proximate to the microfluidic channel;
at least one microfluidic prism is arranged proximate to the second end of the first light conveying structure; and
a first lens structure arranged between the microfluidic channel and the first end of the first light conveying structure, and additionally comprising a second lens structure arranged between the second end of the first light conveying structure and the at least one microfluidic prism, wherein each of the first and second lens structures is a respective fluidic lens having a respective outer wall and a respective internal fluid, wherein at least one of the first and second lens structures is connected to a tap by which the respective internal fluid can be driven into or removed from the respective lens structure, and wherein the first light conveying structure is selected from the group consisting of a waveguide and an optical fiber,
wherein light emanating from the microfluidic channel is provided to the first light conveying structure at the first end, conveyed by way of the first light conveying structure to the second end, and in turn provided to the at least one microfluidic prism,
wherein the at least one microfluidic prism in turn outputs a plurality of portions of the light at a plurality of different frequency ranges, respectively, in a plurality of different directions, respectively.

19. The system of claim 18, wherein the at least one microfluidic prism includes first and second microfluidic prisms, wherein the light provided to the at least one microfluidic prism is incident on the first microfluidic prism, which in turn directs at least some of the light to the second microfluidic prism, which in turn outputs the plurality of portions of the light.

20. The system of claim 18, wherein at least one of the following is true:
the light emanating from the microfluidic channel includes scattered light;
the light emanating from the microfluidic channel includes fluorescent light; and
the light emanating from the microfluidic channel is indicative of light absorption that has occurred due to a presence of material within the microfluidic chamber.

* * * * *

UNITED STATES PATENT AND TRADEMARK OFFICE
CERTIFICATE OF CORRECTION

| | | |
|---|---|---|
| PATENT NO. | : 7,746,466 B2 | Page 1 of 1 |
| APPLICATION NO. | : 12/152665 | |
| DATED | : June 29, 2010 | |
| INVENTOR(S) | : Jessica Godin and Yu-Hwa Lo | |

It is certified that error appears in the above-identified patent and that said Letters Patent is hereby corrected as shown below:

On the Face Page, in Field (56), under "FOREIGN PATENT DOCUMENTS", in Column 2, Line 1, please delete "WO20070403313" and insert -- WO2007040313 --, therefor.

Signed and Sealed this
Third Day of May, 2011

David J. Kappos
*Director of the United States Patent and Trademark Office*